United States Patent
Russell

(10) Patent No.: US 9,486,160 B2
(45) Date of Patent: Nov. 8, 2016

(54) ANALYSING SEATING USING PRESSURE SENSORS

(71) Applicant: XSENSOR Technology Corporation, Calgary (CA)

(72) Inventor: Terence Russell, Calgary (CA)

(73) Assignee: XSENSOR Technology Corporation, Calgary (CA)

( * ) Notice: Subject to any disclaimer, the term of this patent is extended or adjusted under 35 U.S.C. 154(b) by 603 days.

(21) Appl. No.: 13/912,069

(22) Filed: Jun. 6, 2013

(65) Prior Publication Data

US 2013/0332104 A1 Dec. 12, 2013

Related U.S. Application Data

(60) Provisional application No. 61/657,758, filed on Jun. 9, 2012.

(51) Int. Cl.
*A61B 5/103* (2006.01)
*A61B 5/00* (2006.01)

(52) U.S. Cl.
CPC ........... *A61B 5/1036* (2013.01); *A61B 5/6893* (2013.01); *A61B 5/742* (2013.01); *A61B 2562/0252* (2013.01)

(58) Field of Classification Search
CPC .... A47C 31/126; B60N 2/002; A61B 5/024; A61B 5/1126; A61B 5/1036; A61B 5/6893; A61B 5/742; A61B 2562/0252
USPC ...... 702/127, 138, 391; 340/573.1; 600/301, 600/587, 595
See application file for complete search history.

(56) References Cited

U.S. PATENT DOCUMENTS

| | | | | |
|---|---|---|---|---|
| 5,060,174 A | * | 10/1991 | Gross | A47C 31/126 702/139 |
| 5,528,698 A | * | 6/1996 | Kamei | B60N 2/002 250/227.15 |
| 7,378,975 B1 | * | 5/2008 | Smith | A61B 5/1126 340/573.1 |
| 2011/0263950 A1 | * | 10/2011 | Larson | A61B 5/024 600/301 |

* cited by examiner

*Primary Examiner* — John H Le
(74) *Attorney, Agent, or Firm* — Fenwick & West LLP

(57) ABSTRACT

A pressure sensor measures the surface pressure distribution of a body supported by a surface, for example a person sitting on an automotive seating. In one approach, a pressure mapping system presents this pressure data in the form of a pressure map. The pressure map can be aligned to an image of the automotive seating including measurement zones of interest. The measurement zones of interest are mapped onto a human body model, which may include various body zones. In this way, the pressure distribution on different body zones can be visualized and interpreted to assess the performance of the automotive seating.

21 Claims, 8 Drawing Sheets

ANALYSING SEATING USING PRESSURE SENSORS

CROSS-REFERENCE TO RELATED APPLICATION(S)

This application claims priority under 35 U.S.C. §119(e) to U.S. Provisional Patent Application Ser. No. 61/657,758, "Analysing Seating using Pressure Sensors," filed Jun. 9, 2012. The subject matter of all of the foregoing is incorporated herein by reference in their entirety.

BACKGROUND OF THE INVENTION

1. Field of the Invention

This invention relates generally to the detection and analysis of pressure data for automotive seating and other body support systems.

2. Description of the Related Art

The performance of automotive seating and body support systems depends in part on how much pressure and pressure gradients are experienced by different parts of the body. In order to assess support surfaces and compare performance differences due to design changes and material selection, there are industry standard ways to quantify surface pressure information.

A simple pressure map of a seating surface typically provides insufficient information to visualize and standardize the assessment of the impact of pressures on the human body. A more advanced approach is to divide the automotive seating, for example, seat and backrest, into different zones and calculate pressure or other physical measurements for each zone. These zones may be mapped onto a human body model in order to assess the impact of seating pressures, and other metrics, on the body.

In order to accurately map pressure and other physical measurements onto the human body model, the pressure measurements and seating zones should be aligned to the human body model. However, manually separating the pressure map data into seating zones and mapping those against the human body model is a lengthy process that is prone to error.

Therefore there is a need to automate the measurement and alignment of seating features, pressure measurements and human body models.

BRIEF DESCRIPTION OF THE DRAWINGS

The invention has other advantages and features which will be more readily apparent from the following detailed description of the invention and the appended claims, when taken in conjunction with the accompanying drawings, in which:

DETAILED DESCRIPTION OF THE PREFERRED EMBODIMENTS

Figure 1:
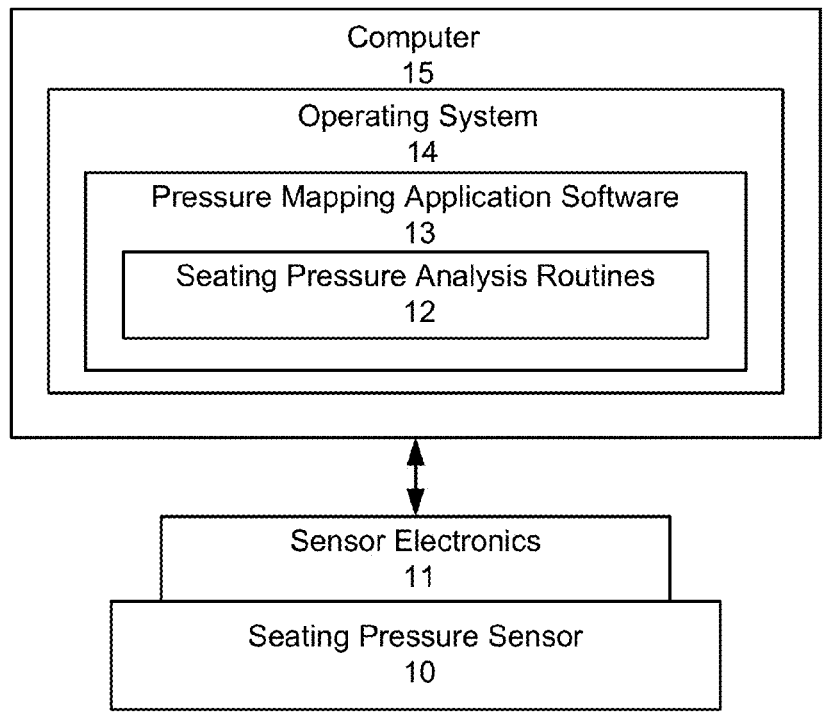
FIG. 1 is a diagram of a pressure mapping system.

A pressure sensor measures the surface pressures caused by a body supported by a surface, for example a person sitting on automotive seating. In one approach, a pressure mapping system presents this pressure data in the form of a pressure map. The pressure map can be aligned to an image of the automotive seating including measurement zones of interest. The measurement zones of interest are mapped onto a human body model, which may include various body zones. In this way, the measured pressures on different body zones can be calculated, visualized and interpreted to assess the performance of the automotive seating.

In order to do this, the individual pressure measurements within the pressure map are mapped to specific body zones. In one implementation, this is achieved as follows. An image of the seating is provided and the pressure sensor is mapped to the seating image. In this way, the location of individual pressure sensing elements with respect to the seating is known. The seating is also mapped into different seating zones and these seating zones are mapped to a human body model. For example, each seating zone may correspond to a specific body zone in the human body model. In this way, locations on the seating (and, hence, individual pressure sensing elements) can be mapped to specific body zones. Thus, the pressure sensor and the pressure measurements are aligned to the body zones through use of the intermediate zoned seating image.

In another aspect, the pressure map, seating image and seating zones, and the body map are automatically (or semi-automatically) aligned based on analysis of the pressure map. For example, the pressure map may be analyzed to extract certain features that are used to aid alignment. By automatically aligning the data, the initial set up required by the operator can be significantly reduced, resulting in time savings and more consistent measurements.

In another aspect, the automatic measurements that are performed are selected by the user. They may be presented as individual pressure map frames, statistically analyzed over multiple frames and/or compared to historical data. Higher quality seating typically will provide greater contact area, lower peak pressures, lower pressure gradients, and smaller pressure distributions and loading around key body features such as the iliac tuberosity, sacrum, hips, and legs.

The ability to quickly perform measurements and compare historical data facilitates rapid and more consistent development of automotive seating products and other body support products. This capability can also be used for quality assurance. For example, a pressure sensor can be mounted on a buttock and back form and a known load applied to the seating as a final QA test before installing the automotive seating in the vehicle. If pressure measurements are not within specification then the seating is rejected. For designers, pressure mapping can be a useful tool for testing out new cushions, fabrics, and bolster designs. Design decisions and material selections can be based in part on the comparison and evaluation of measurements automatically obtained by the pressure mapping system.

The system shown in FIG. 1 includes three major components, the seating pressure sensor(s) (10), the sensor electronics unit (11), and the computer (15). The computer includes software subcomponents including the operating system (14), the application software (13), and the pressure analysis routines (12). As used in this document, the term "seating" will be used as a general term while "seat" will refer to seating that supports the buttocks when a human is sitting. Thus, seating includes seats, but also includes backrests, headrests, footrests, armrests, etc.

Automotive Seating Sensor.

A seating pressure sensor (10) can come in various sizes to suit a wide range of seating sizes and shapes. Typically, there is one pressure sensor on the seat and another pressure sensor on the backrest. For example, automotive seating typically has seat sensing areas ranging from 18"×18" to 30"×30", or preferably 24"×24", and backrest sensing areas ranging from 12"×18" to 30"×40", or preferably 20"×32". Other sensing areas are possible to accommodate larger seating areas, such as seating for heavy trucks, industrial, and mining vehicles, or smaller seating areas, such as forklifts, rider mowers, boat seating, horseback saddles or even motorcycle seating. Other non-automotive examples of seating applications include train seating, airplane seating, dental chairs, home seating, wheelchairs, and office chairs.

Each pressure sensor (10) contains an array of individual pressure sensing elements. Seating sensor resolution is typically 0.010" to 0.100" pitch, or preferably 0.050" pitch. A sense 1 is an individual sensor within a sensor array. Automotive seating sensor arrays are typically 36 sensels× 36 sensels to 64 sensels×64 sensels, or preferably 40 sensels×40 sensels. Backrest sensor arrays are typically 24 sensels×36 sensels to 64 sensels×128 sensels, or preferably 40 sensels×64 sensels.

Additional sensors may also be added to extend or enlarge the seating sensing area. For example, an additional 8"×4" sensor could be placed on the headrest to capture information on support or proper fitting of the headrest. For captain's chairs, such as those found in a recreational vehicle, 18"×3" sensors could be placed on the armrests. An 18"×24" foot sensor could also be placed on the floormats to measure heel and foot pressure.

Seating pressure sensors preferably are thin and flexible sensors that are designed to conform to the shape of the seat and backrest. They are typically covered with a light fabric, for example nylon taffeta, and may incorporate buckles, straps, or other methods of attaching the sensor to the seating. The sensor cover material may be silk screened on one side with a grid representing the location of the individual sensels within the sensor array. This assists with the alignment of the sensor and thereby improves the accuracy of the measurement.

Figure 2:
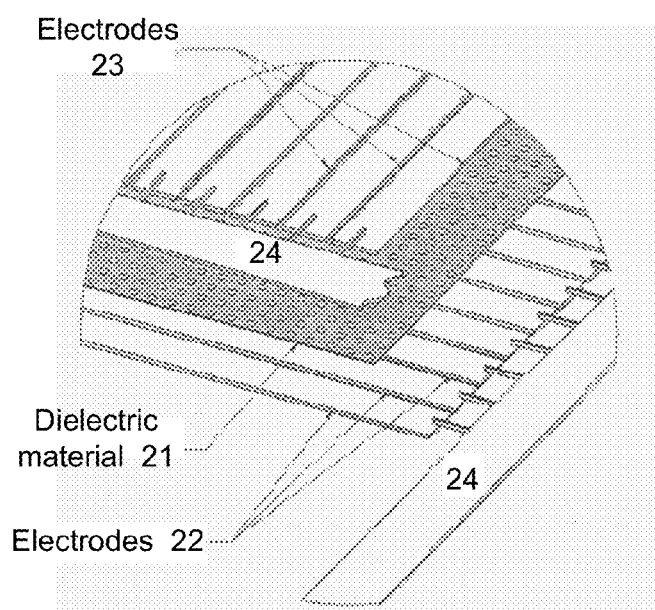
FIG. 2 is an exploded view of a capacitive pressure sensor.

Examples of seating pressure sensors include resistive pressure sensors, fibre-optic pressure sensors, or preferably capacitive pressure sensors. FIG. 2 illustrates the construction of an example capacitive pressure sensor. The sensor includes column electrodes (23) onto which a sinusoidal electrical signal is injected and row electrodes (22) where an attenuated sinusoidal signal is detected. The row and column electrodes are constructed of strips of electrically conductive material such as copper strips, aluminum strips, tin strips, or preferably conductive fabric or flexible circuit. The row and column electrodes are separated by a compressible dielectric material (21) such that the dielectric compresses according to the pressure applied to the surface of the sensor. An electrical signal is injected on a column electrode and is then attenuated as it passes through the dielectric material to the row electrode where the attenuated signal may be detected. The attenuation of the signal depends on the amount of dielectric compression resulting from the applied pressure. The detected signal can be measured by the sensor electronics and converted to a pressure value using a calibration process. The row and column electrodes are connected to the sensor electronics using a ribbon cable (24) or other electrically conductive wiring harness, for example, discrete wires, conductive fabric, printed circuit board, or preferably, a flexible circuit.

Sensor Electronics Unit.

Figure 3:
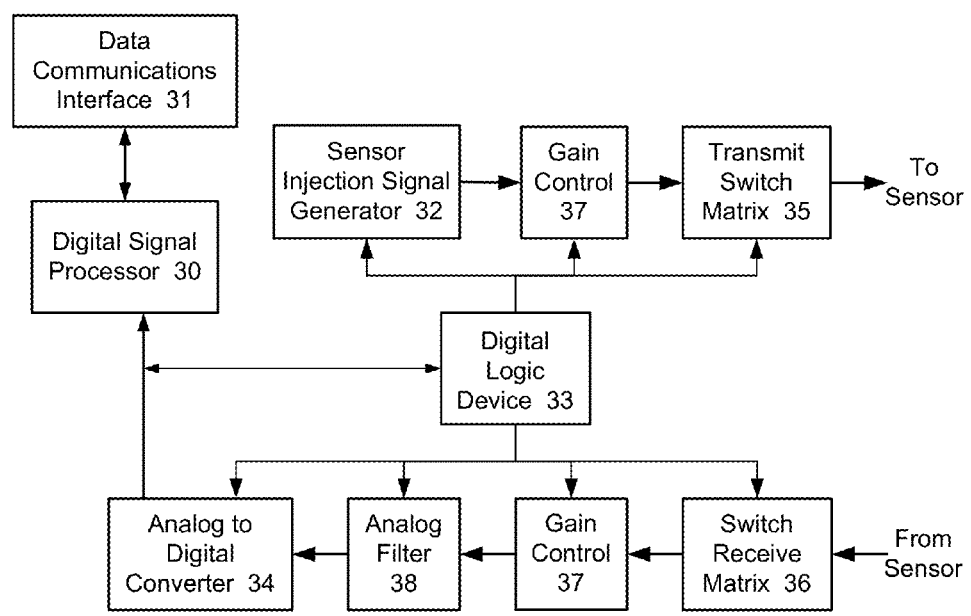
FIG. 3 is a block diagram of a sensor electronics unit.

An example sensor electronics unit shown in FIG. 3 includes a digital signal processor (DSP) (30), injection signal generation and control (32), (37), (35), signal detection and control (36), (37), (38), (34), a digital logic device (33), and a data communications interface (31).

The DSP (30) executes firmware that is designed to receive control messages from application software running on a PC via the data communications interface (31). The control messages include measurement requests that contain coordinates for an individual sensing element (sensel) within the pressure sensor array. The DSP (30) selects a column for the injection signal and a row for signal detection. The detected signal is then converted from analog to digital (34) for measurement processing by the DSP (30). The measurement is then passed back to the application software via the data communications interface (31).

The DSP (30) may be a standalone device or include external memory such as Random Access Memory (RAM), Read Only Memory (ROM), or any other commonly used memory device. Memory devices can be accessed either serially or via parallel data bus.

The sensor injection signal generation block (32) is an electronic device or circuit used to create a sinusoidal injection signal at a selectable frequency. The injection signal can be in the range of 50 Khz to 5 Mhz, or preferably 250 Khz or 100 Khz.

The gain control block (37) is an electronic device or circuit used to adjust the amplitude of the injection signal. The gain setting is controlled by the DSP (30) via the digital logic device (33). The amplified injection signal is connected to the transmit switch matrix (35). The DSP (30) configures the digital logic device (33) to enable the appropriate switch in the switch matrix in order to select a sensor column for transmitting the injection signal.

The injection signal passes through the pressure sensor and is detected on a row selected using the receive switch matrix (36). The sensor row is selected by the DSP (30) via the digital logic device (33) and the selected signal is connected to the gain control block (37) for amplification.

An analog filter (38) removes signal noise before the analog to digital converter (ADC) (34). The analog filter is an electronic device or circuit that acts as a band pass or low pass filter and only passes frequencies near the injection signal frequency. For example, if the injection signal has a frequency of 250 Khz the filter only passes frequencies in the range of 200 Khz to 350 Khz and thereby rejects other interfering signals that are not within the pass band. The analog filter can be designed to accommodate pass bands of variable frequency spreads where tighter frequency spreads more effectively filter interfering signals.

The ADC (34) is periodically sampled by the DSP (30) in order to acquire sufficient samples for performing a measurement calculation. For example, 12, 24, 48, 96, or 192 samples can be acquired before performing a measurement calculation on the samples. The DSP (30) can also execute firmware to perform additional digital filtering in order to further reduce the frequency spread of the pass band and more effectively filter interfering signals. Digital filtering requires more samples from the ADC (34), for example 256, 1024, 2048, or preferably 512 samples.

The data communications interface (31) passes data between the DSP (30) and the application software running on a PC. The interface includes electronic devices or circuitry to perform wired or wireless communication. Examples of wired communication include RS232 serial, Universal Serial Bus (USB), Ethernet, fibre-optic, or any other serial or parallel data communication technology. Examples of wireless communication include, Zigbee, Bluetooth, WiFi, Wireless USB, or any other wireless data communication technology.

The digital logic device (33) includes electronic devices or circuitry, for example complex programmable logic devices (CPLD), field programmable gate arrays (FPGA), application specific integrated circuits (ASIC), or discrete logic devices.

Application Software.

In this example, the pressure mapping application software (13) runs on a standard computer device, for example, a desktop computer, laptop, pad computer, tablet, touchscreen kiosk, personal data assistant, smart phone, handheld computer, server, or mainframe computer.

The application software (13) runs with a standard computer or embedded operating system (OS) (14) such as Linux, embedded Linux, NetBSD, WindowsCE, Windows embedded, Mac OS, iOS, Android, Windows8, QNX, Blackberry OS, or preferably, Windows7 or WindowsXP.

The application software performs basic functionality such as data messaging with the sensor electronics (11), conversion of measurements from the sensor electronics (11) to calibrated pressure values, display processing and control for the pressure map and user interface, calibration management and control, and numerous user-initiated advanced measurement processing and image processing techniques.

The application software performs a number of automated measurements that are derived from the pressure data. For example, center of pressure can be calculated for the entire pressure map or for smaller groups of sensels. In another example, average pressure can be calculated over the entire pressure map or within a smaller user selected area. In another example, contact area can be calculated within a pressure map by determining the number of sensels that are above a pressure threshold. In another example, a load calculation can be automatically performed using the pressure data and the contact area. Automated measurements specific to automotive seating can also be performed.

Automotive Seating Analysis Process

In one approach to automating seating sensor pressure measurements, the pressure sensor (and hence the pressure map) is aligned with the seating image and the seating measurement zones. This alignment process can be performed manually by having the user identify alignment points on the pressure map or automatically by having the software detect alignment markers or analyze biometric data. Once the three images are aligned, the measurements can be made with a high degree of accuracy. In one variation, the zones of interest are also customizable.

Figure 4:
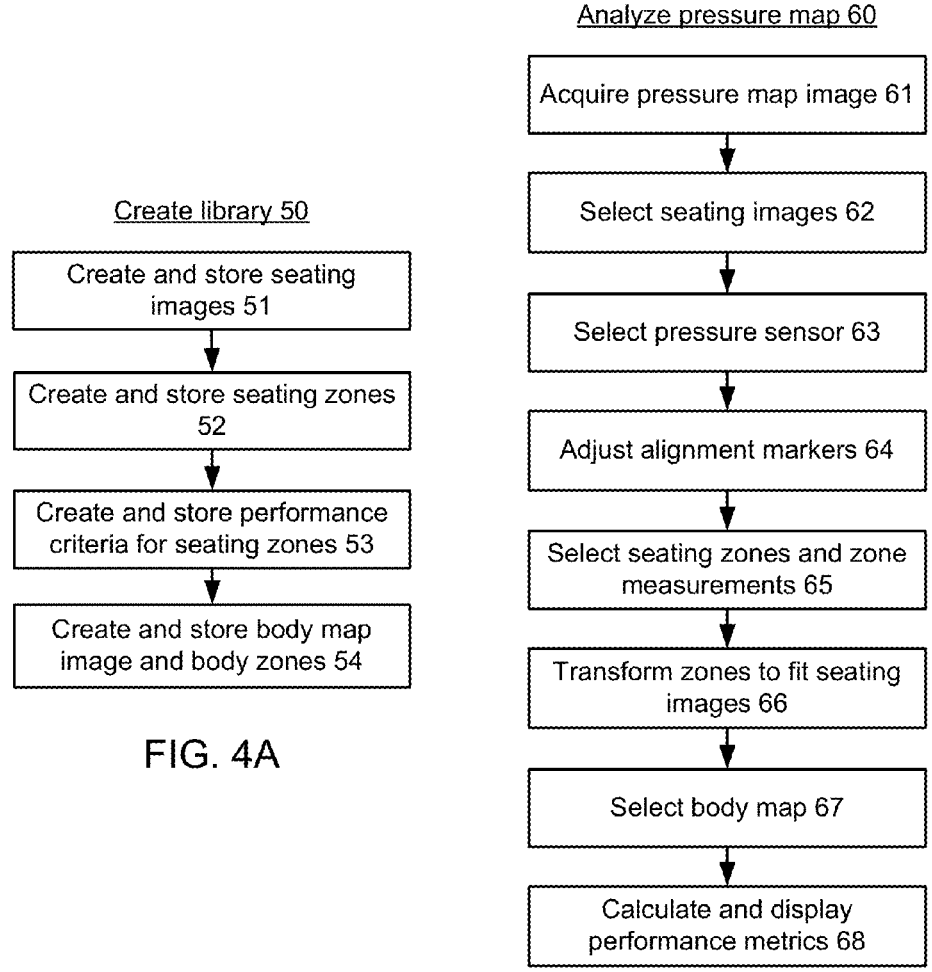
FIGS. 4A and 4B are flow diagrams of an automotive seating analysis process.

FIGS. 4A and 4B are flow diagrams of an example automotive seating analysis process. This process can generally be broken into two phases: creating (50) a library of information (i.e., initial setup) and analysis (60) of measured pressures.

FIG. 4A shows an example process for creating (50) a library of useful information. This library includes images (51) of seating to be analyzed, seating zones (52) defined for the different seating images, acceptable values for various performance metrics (53), and human body models including different body zones (54). The library is useful in order to set up the analysis tool for the seating to be analyzed. The seating image library can be created (51) using digital photographic images of the automotive seating to be analyzed. The seating zone library is created (52) using a zone editor tool to divide the seat and backrest areas (or other seating areas) into specific zones of interest. For each zone, thresholds or other performance criteria may be entered (53) to be used as pass/fail criteria for automated measurements. The pass/fail criteria is particularly useful for quality assurance testing in manufacturing facility production lines but may also be used for research activities as well. A body map image is created (54) using an electronic graphic illustrator. The body map image includes different zones of interest that correspond to the seating zones. Thus, the analysis based on seating zones can be displayed on the corresponding body zones on the body map.

FIG. 4B shows an example process for analyzing (60) a pressure map. When analyzing an automotive seating, the process typically begins by acquiring (61) an image of a pressure map recorded in a session file. To configure the analysis tool, the seating images (e.g., seat and backrest images) for the seating in question are selected (62) from the library of seating images. The pressure map image is scaled and aligned (63,64) with the seating image, for example by entering the marker coordinates for the sensor, by using a live alignment tool, by using automated marker detection, and/or by using biometric data analysis to automate the alignment. The zone groups for the seating are selected (65) and the type of measurement for the zone group is selected (65). Optionally, the zone group can be transformed (66) to align it with the seating image. The body map image is selected (67) from the library and the zone measurements to be displayed on the image are also selected (67). The selected performance metrics are calculated and displayed (68).

Once this process is completed, the pressure map can be advanced to other frames (i.e., other measurements) for comparative analysis. For example, subjects with different body types can be pressure mapped on the automotive seating being analyzed. As the pressure map frames are advanced from one subject to the next, the zone measurements can be compared or monitored to see if they remain within the predetermined measurement thresholds created with the zone editor. In another example, the automotive seating could be subjected to shocks and vibrations. As the pressure map frames are advanced in time the measurements can be analyzed to evaluate the pressure measurement response to the shocks and vibrations.

The steps shown in FIGS. 4A-4B will be described in more detail, using a specific example.

Library Creation (51-54).

In FIG. 4A, a library of seating images (51) and a library of seating zones (52) is created. The seating image and seating zone libraries may be created by the seating designer or manufacturer, or can be created or modified by the user of the software. The seating and seating zones may be generic, or preferably tailored to specific seating.

In one approach, a digital image of the seating (e.g., seat and backrest) are created (51) using a digital camera or by scanning a photographic image. The image is added to the library folder in a standard image file format, for example, .jpg, .png, .bmp, .eps, .gif, .tif, or, .xbm.

Figure 5:
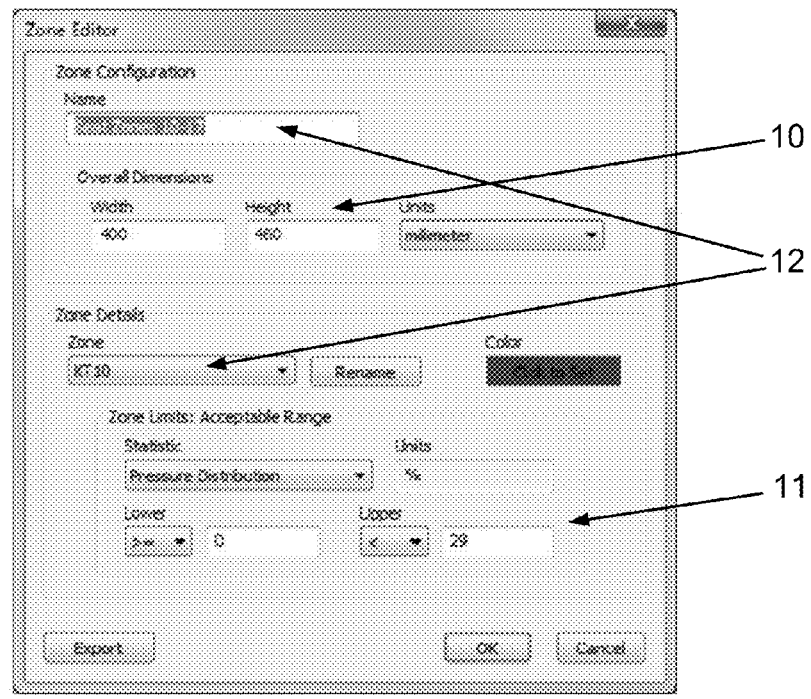
FIG. 5 is an example screen of a seating zone editor used to create seating zones for various seating designs and constructions.

In this example, the seating zones are created (52) and performance metrics defined (53) using a seating zone editor that allows dimensions to be entered for each zone. An example of one screen of a seating zone editor is shown in FIG. 5. In the example shown, the seating zones are a 17-zone configuration based on industry standard zone configurations. However, other configurations, for example a 15, 19, or 21 zone configuration, may also be created. Each zone is selected (12), the dimensions (10) for the zone are entered, and the zone measurement limits (11) are also entered. This is just one example of how to define seating zones.

In more detail, this 17-zone configuration can be broken into two parts: zones 1-11 for the backrest and zones 10-17 for the seat. FIG. 5 shows the configuration of zone KT10 (identified by reference numeral (12)) within seat zones 10-17. The position of this seating zone relative to the other zones is defined by the industry standard zone configuration. However, the size of the zone may vary from seating to seating. The zone editor allows the user to define (10) the size of zone KT10 as 400×460 mm in this example. The acceptable range for pressure distribution in zone KT10 is defined (11) as 0-29%. The other 16 zones can be configured in a similar manner.

Acquire Pressure Map Images (61).

Figure 6:
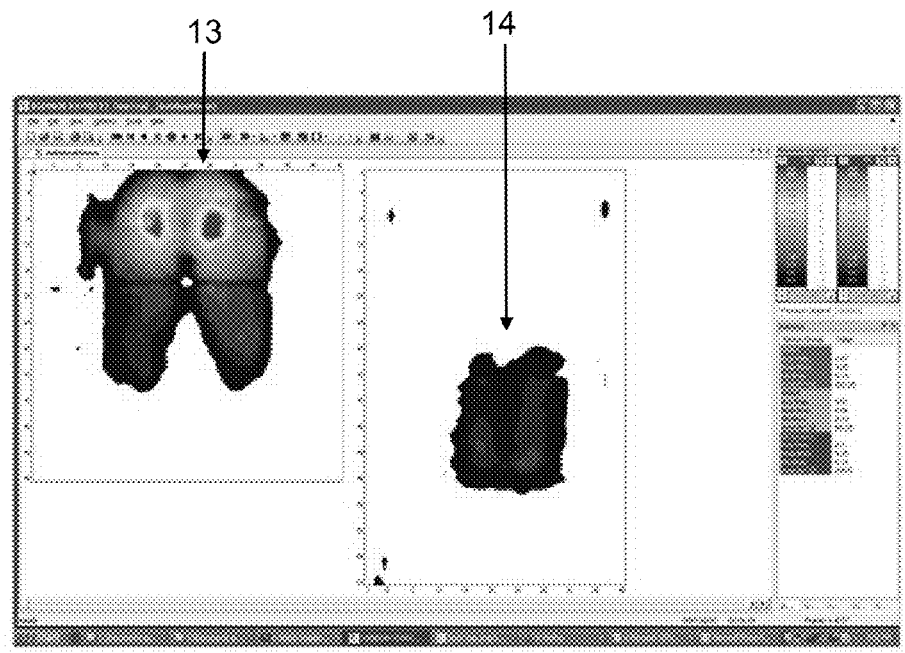
FIG. 6 is an example of a pressure map for an automotive seat pressure sensor and backrest pressure sensor.

In FIG. 6, an example of pressure map images are shown for the seat (13) and backrest (14). These images are acquired using a pressure mapping system. The pressure map may be captured as a single frame, multiple frames, or frames recorded continuously over a period of time. In another example, a pressure map image is acquired from a single pressure sensor (rather than the two pressure sensors shown in FIG. 6), for example only a seat pressure sensor or only a backrest pressure sensor. In another example, pressure map images are acquired by two or more pressure sensors that can be placed at locations of interest on the automotive seating, such as the headrest, armrests, footrests, seat, and backrest.

Seating Image Selection and Alignment (62-64).

Figure 7:
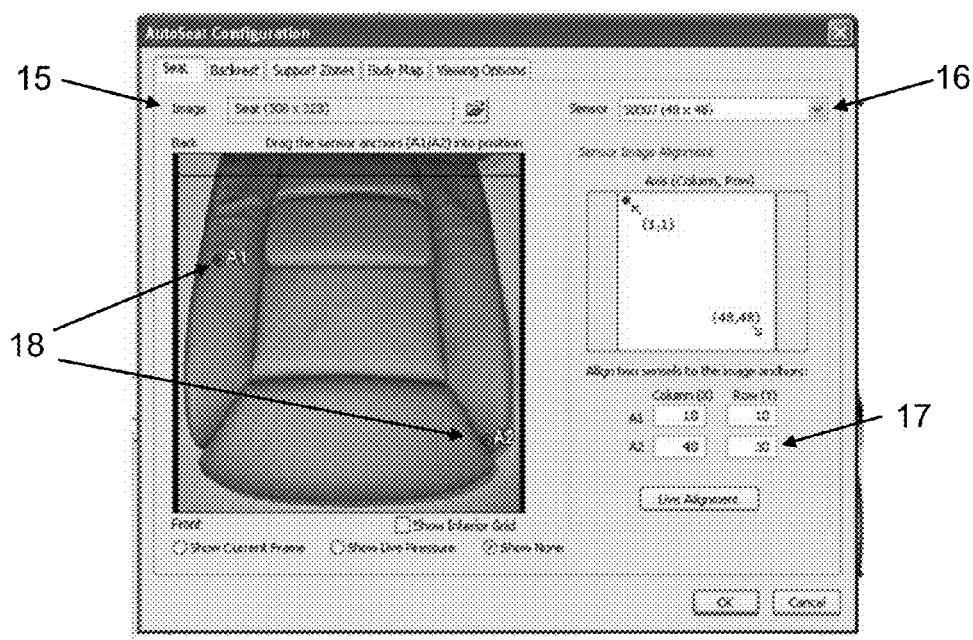
FIG. 7 is an example illustrating manual alignment of a pressure sensor with seating.

In FIG. 7, an image of the seating in question (i.e., the seating corresponding to the acquired pressure map) is selected (15,62) from the image library. The pressure sensor measuring pressure on the seating is selected (16,63) from the connected sensor list. In FIG. 7, the seating is a seat (rather than the backrest) and the pressure sensor is a 48×48 sensor.

Next, the positioning of the pressure sensor relative to the seating is determined (64), with the use of alignment anchor points (18) A1 and A2 in this example. The anchor points will be located on the seating and also on the pressure sensor, thus determining how the pressure sensor aligns to the seating. On the lefthand side of FIG. 7, the positions of anchor points (18) A1 and A2 on the seating are identified by clicking and dragging the anchor points on the seating image. The anchor points preferably are defined by easy to identify features on the seating. For example, anchor point A2 may be defined as located on the seam between the two seat pieces and half an inch in from the edge.

The anchor points are also located on the pressure sensor. If the location of the anchor points on the pressure sensor are known, they can be identified by manually entering (17) the sensel coordinates. For example, some pressure sensors have a grid that is silkscreened on the sensor cover, so the sensel coordinates can be determined from the grid. On the righthand side of FIG. 7, the sensel coordinates of anchor point A2 are known as (40,30) and they are manually entered.

Figure 8:
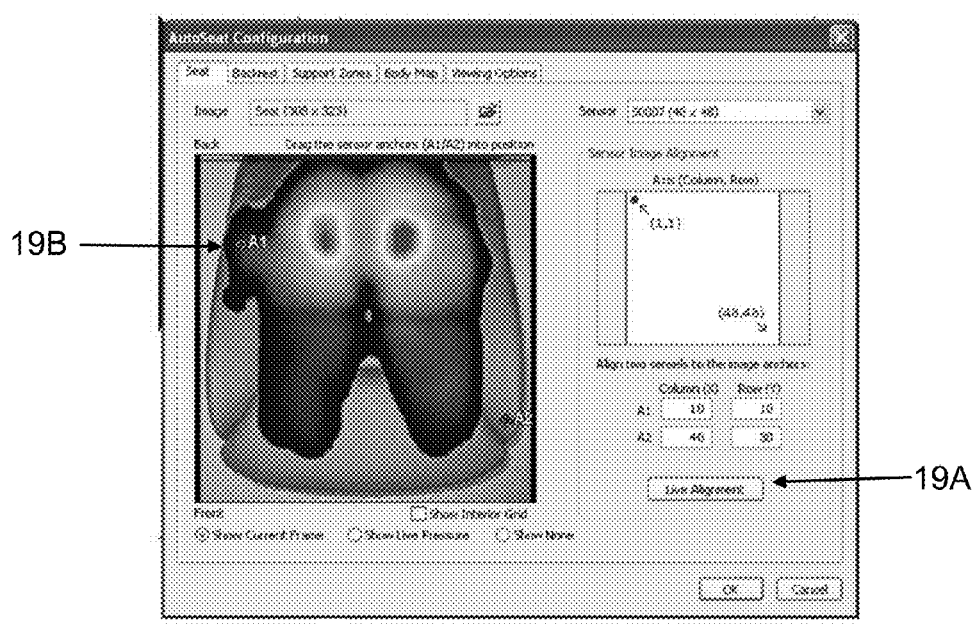
FIG. 8 is an example illustrating assisted alignment of a pressure sensor with seating.

In FIG. 8, the alignment of the pressure sensor to the seating is achieved with software assistance. The user invokes this mode by clicking the Live Alignment button (19A). The alignment tool prompts the user to apply pressure at each anchor point on the seating and maintain this pressure for a period of time sufficient for the pressure point to be automatically located by the software. For example, for A2, the user finds the location along the seam that is half an inch in from the edge and applies pressure at that location. The software determines which sensels are being pressed. The sensel coordinates for the anchor points are updated with the automatically detected sensel coordinates.

This process is repeated for the backrest or other pressure sensors.

Seating Zone Selection and Alignment (65-66,68).

Figure 9A:
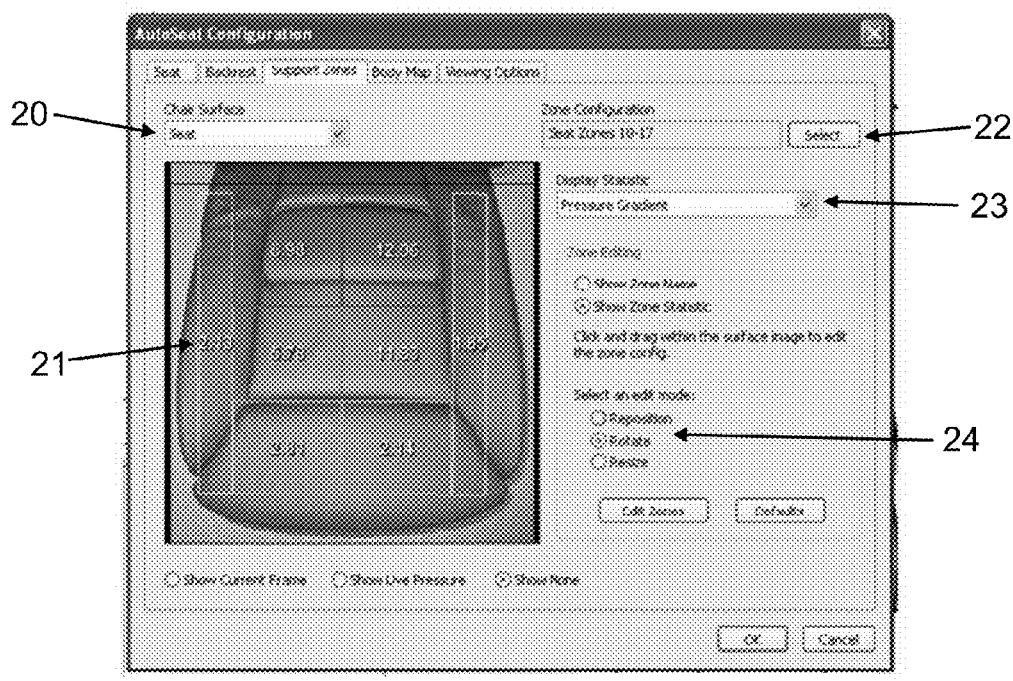
FIGS. 9A and 9B are examples of a seating zone selection, configuration, and alignment process for a seat and backrest, respectively.

In FIG. 9A, the seat surface is selected (20) for zone alignment, the zone configuration is selected (22) from the zone library, and the seating zones (21) then appear overlaid on the seating image. The zone configuration may be transformed (24) to align it with the seating image. In this example, the alignment tool permits rotation, resizing, and repositioning of the zone configuration for best fit on the seating image.

The measurement type (23) is selected for the zone configuration. The associated performance metrics (21) are calculated (68) based on the pressure map and displayed in the seating zones overlaid on the seating image. The previous alignment process described in FIGS. 7-8 defines where each individual pressure measurement is located on the seating. The zone configuration defines which part of the seating lies within each seating zone. Combining this information yields which individual pressure measurements fall within each seating zone. The performance metrics can be calculated for each zone based on the applicable pressure measurements.

Figure 9B:
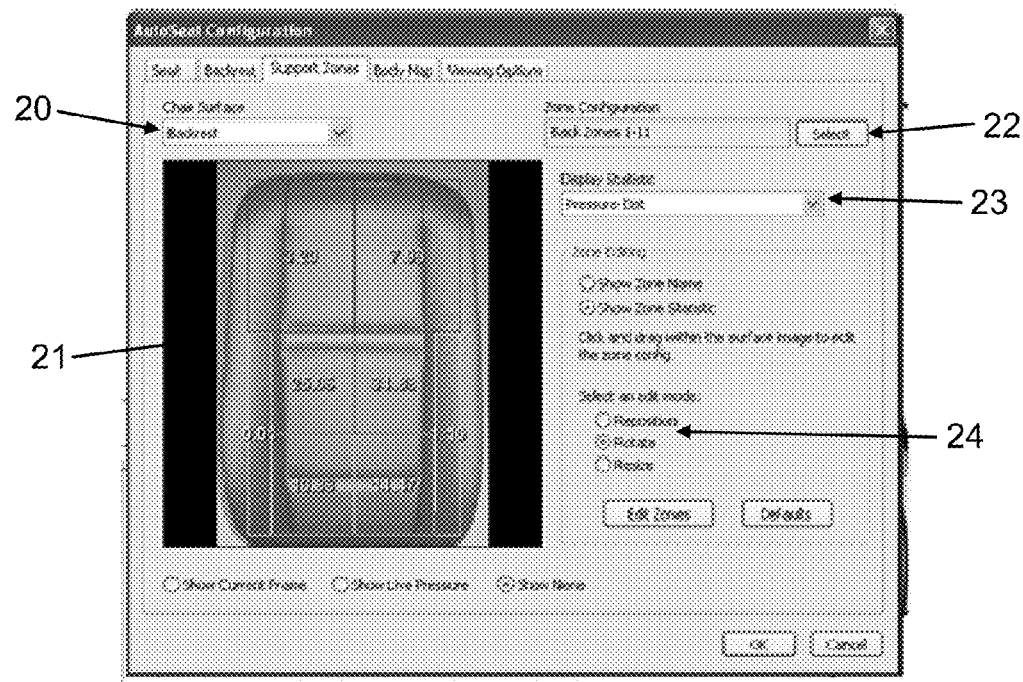

This process is also performed for the backrest zone configuration, as shown in FIG. 9B.

Body Map Selection.

Figure 10:
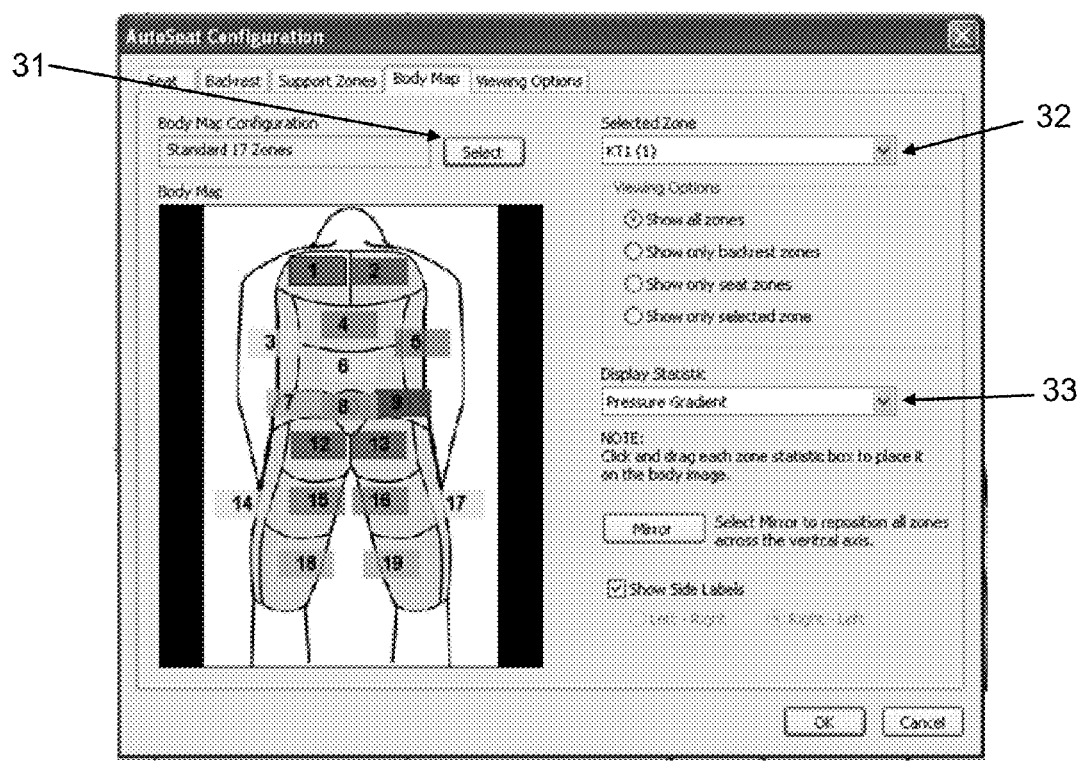
FIG. 10 is an example of a body map selection and configuration process for selecting a body map, the body zones to be displayed on the body map, and the measurements to be displayed for the body zones on the body map.

In FIG. 10, a body map image is selected (31) from the body map library and the zones to be displayed on the body map are selected (32). For example, a single zone of interest can be selected, zone groups can be selected or preferably all zones in the zone configuration can be selected for display. The measurement type (33) is selected for display on the body map. The seating zones correspond to the body zones, so the performance metrics for the body zones can be calculated from the measured pressures. In this example, there is roughly a one-to-one correspondence between seating zones and body zones.

Measurement Options.

A number of different measurements can be automatically performed and displayed for the zones on the seating images and body map. For example, measurements could include peak pressure in the zone, average pressure for the zone, contact area for the zone, load (average pressure×area of zone), pressure distribution for the zone and pressure gradient for the zone. In another example, measurements can be automatically computed, such as ratios comparing contact area to non-contact area, ratios comparing specific zone measurements, statistical comparisons of zone measurements, such as mean, median, and standard deviation over individual zones, groups of zones or the entire zone configuration. In another example, statistical comparisons of zone measurements can be made over multiple pressure map frames for selected frames or for a continuous block of frames.

Figure 11:
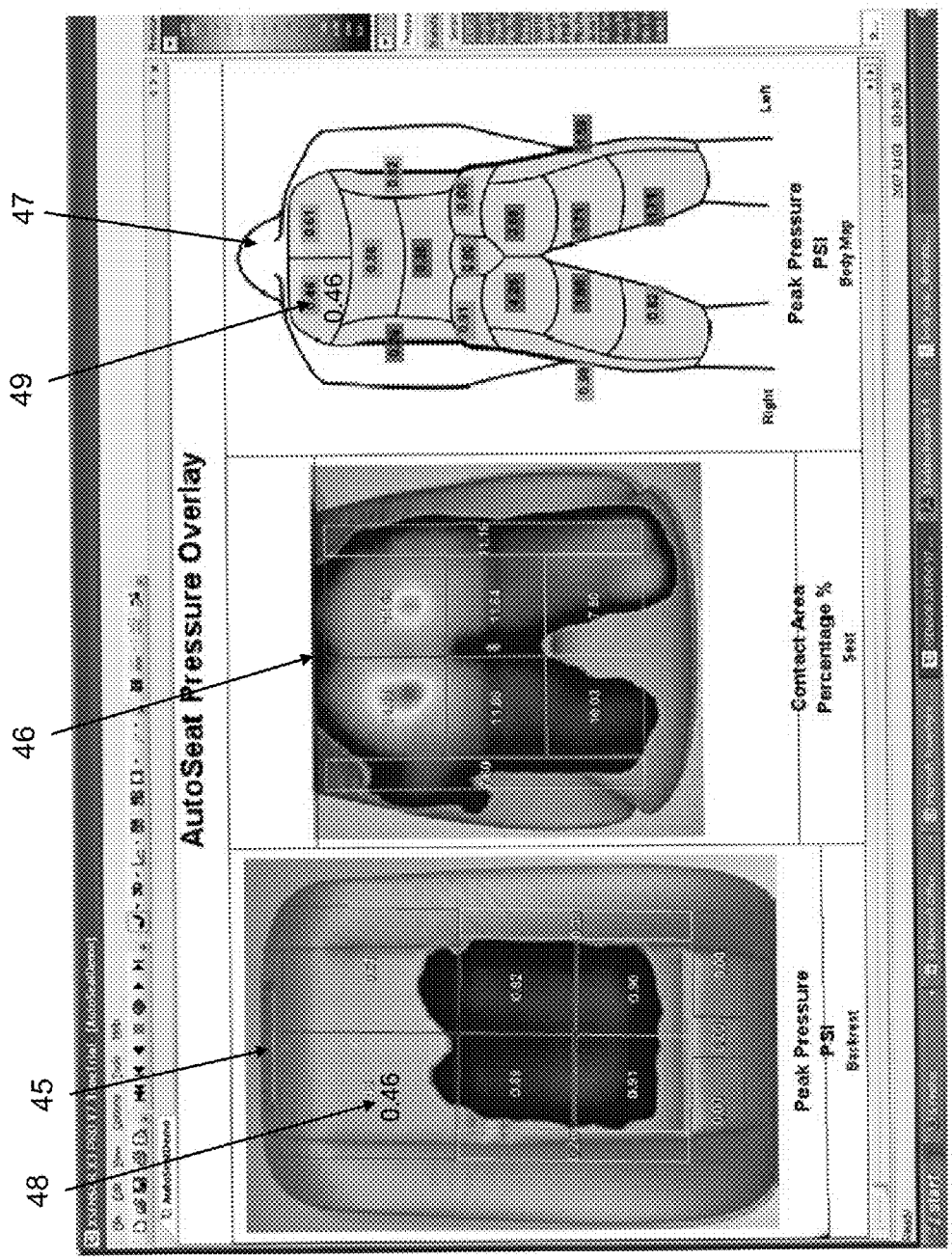
FIG. 11 is an example of a user interface for a pressure mapping system, displaying seating zones for a seat and a backrest, and corresponding body map measurement information.

In FIG. 11, an example is provided of the display of measurements for the seat pressure map (46), the backrest pressure map (45), and the body map (47). Note that the zones on the seat and backrest are mapped onto the body map image. It can be seen that the peak pressure in the top left backrest zone (48) is 0.46PSI and this corresponds to the measurement shown in the top left shoulder of the body map (49). Note that the user can also invert the body map such that it maps more directly onto the seating image, simulating the body sitting in the seating. In the example shown in FIG. 11, peak pressure is displayed for the backrest zones, contact area is displayed for the seat zones, and peak pressure is displayed for the body map. Any combination of measurements can be selected for display on the three images (seat, backrest, body map). On the body map, measurements that fall outside the measurement zone limits created with the zone editor are displayed in red. Measurements that fall within the measurement zone limits are shown in green.

The pressure distribution for a zone is the ratio of the zone's load (average pressure×zone area) to the load across the entire pressure sensor area. The unit of measure is percent, %. The pressure gradient for a zone is a measure of how rapidly the pressure gradient is changing across the zone. This provides an indication of the magnitude of shear force within the zone. Pressure gradient can be computed as follows:

1. The pressure is summed across each row of sensels that traverses the zone.
2. Compute the delta between the summed pressures for each adjacent row in the zone.
3. Calculate the slope of the pressure delta for each row in the zone by dividing the summed pressure delta by the distance between sensels, for example, 0.5" for a standard seating sensor.
4. The highest magnitude slope value is displayed as the Pressure Gradient value. The unit of measure is pressure/distance, for example PSI/inch.

The automated measurements are displayed in standard units for pressure, distance, area and ratios. For example, pressure measurements may be displayed in units of pounds per square inch (PSI), millimeters of mercury (mmHG), atmospheres (atm), inches of water (in H2O), kilogram force per square centimeter (kgf/cm2), grams per centimeter squared (g/cm2), kilopascals (kPa), millibars (mbar), Newtons per square centimeter (N/cm2), Newtons per square meter (N/m2), and any other common unit of measure for pressure. In another example, units of distance may be displayed as inches (in), feet (ft), yards (yds), millimeters (mm), centimeters (cm), meters (m), or any other common unit of measure for distance. In another example, units of area may be displayed as square inches (in2), square feet (ft2), square yards (yds2), square millimeters (mm2), square centimeters (cm2), square meters (m2), or any other common unit of measure for area.

Automated Alignment.

The automotive seating analysis process described above performs automated measurements but the process described for aligning the pressure map, seating image, seating zones and body map are manual or semi-automatic. The alignment process can also be automated, for example by using the alignment markers illustrated in FIGS. 7 and 8.

In an example of a semi-automated process, the alignment tool instructs the user to apply pressure at the alignment points on the seating and then the software detects the applied pressure and automatically aligns the seating image to the pressure map/pressure sensor. In one example, the alignment is automatically performed by fixing pressure markers on the pressure map at the alignment points on the seating. The pressure markers can be weights, or preferably clamping devices, designed to provide point pressure at the alignment points. With this technique the automatic alignment is carried out in a similar fashion to the semi-automatic alignment that requires the user to apply the pressure.

In another example, the alignment process can be fully automated by analyzing biometric information in the pressure map and using this information to align the pressure map image to the seating image. For example, the location of the hips, iliac tuberosities (IT's), sacrum, and IT bands can be used to automatically scale and position the pressure map image on the seating. Information regarding the test subject's measurements, for example, thigh width, distance between the IT's, and distance between the hips is typically used.

In yet another example of automated alignment, historical pressure data can be referenced to align the sensor map to the seating image. For example, a test subject that has been previously tested on this seating can have their pressure map matched to a library of pressure maps to determine the alignment for the test subject. Test subjects with closely matching biometric data could also have their pressure map and seating images aligned automatically. Therefore, a large library of pressure maps for each type of automotive seating surface could be used to automatically match and align images for new test subjects.

Although the detailed description contains many specifics, these should not be construed as limiting the scope of the invention but merely as illustrating different examples and aspects of the invention. It should be appreciated that the scope of the invention includes other embodiments not discussed in detail above. Various other modifications, changes and variations which will be apparent to those skilled in the art may be made in the arrangement, operation and details of the method and apparatus of the present invention disclosed herein without departing from the spirit and scope of the invention as defined in the appended claims. Therefore, the scope of the invention should be determined by the appended claims and their legal equivalents. Furthermore, no element, component or method step is intended to be dedicated to the public regardless of whether the element, component or method step is explicitly recited in the claims.

What is claimed is:

1. A computer-implemented method for analyzing automotive seating comprising a computer system automatically performing the steps of:

displaying a seating image to a user;

providing a user interface to allow the user to graphically locate anchor points on the displayed seating image;

receiving a signal including a location of the anchor points on a pressure sensor, the pressure sensor having an array of individual pressure sensing elements used to measure pressures on the seating;

accessing a pressure map of the pressures measured by the pressure sensor;

determining a first mapping of locations on the pressure map to locations on the seating, based on the location of the anchor points on the pressure sensor and on the seating image; and calculating performance metrics for the seating, based on the pressure map and the first mapping of the pressure map to the seating.

2. The method of claim 1 wherein the seating is divided into seating zones; and the step of calculating performance metrics for the seating comprises calculating performance metrics for the seating zones.

3. The method of claim 1 further comprising:
accessing a second mapping of the seating to a human body model; and
calculating performance metrics for the human body model, based on the performance metrics calculated for the seating and on the second mapping of the seating to the human body model.

4. The method of claim 3 wherein the seating is divided into seating zones, the step of calculating performance metrics for the seating comprises calculating performance metrics for the seating zones, the human body model is divided into body zones, the second mapping of the seating to the human body model includes a third mapping of seating zones to body zones; the method further comprising:
calculating performance metrics for the body zones, based on the performance metrics calculated for the seating zones and on the third mapping of the seating zones to the body zones.

5. The method of claim 1 wherein the step of receiving a location of the anchor points on a pressure sensor comprises:
receiving coordinates of the anchor points input by the user.

6. The method of claim 1 wherein the step of receiving a location of the anchor points on a pressure sensor comprises:
instructing the user to apply pressure to the anchor points; and
calculating the location of the anchor point on the pressure sensor based on the user's applied pressure measured by the pressure sensor.

7. The method of claim 1 wherein the performance metric is a measure of pressure.

8. The method of claim 1 wherein the performance metric is a measure of pressure gradient.

9. The method of claim 1 wherein the performance metric is a measure of pressure distribution.

10. The method of claim 1 wherein the performance metric is a measure of contact area.

11. The method of claim 1 wherein the seating includes a seat and a backrest, and the seating image includes an image of the seat and a separate image of the backrest.

12. The method of claim 1 wherein the seating includes at least one of a headrest, an armrest, a footrest and a floormat area.

13. The method of claim 1 wherein the pressure sensor is a capacitive pressure sensor.

14. The method of claim 1 wherein the seating image is selected from a library of images of different seating.

15. The method of claim 14 wherein the library further comprises a division of the different seating into seating zones.

16. The method of claim 14 further comprising:
accessing a second mapping of the seating to a human body model, the human body model accessed from a library of human body models; and
calculating performance metrics for the human body model, based on the performance metrics calculated for the seating and on the second mapping of the seating to the human body model.

17. The method of claim 1 further comprising:
displaying the calculated performance metrics overlaid on the seating image.

18. The method of claim 1 wherein the seating is divided into seating zones; and the step of calculating performance metrics for the seating comprises calculating performance metrics for the seating zones, the method further comprising:
displaying the calculated performance metrics overlaid on an image of the seating zones.

19. The method of claim 1 further comprising:
accessing a second mapping of the seating to a human body model;
calculating performance metrics for the human body model, based on the performance metrics calculated for the seating and on the second mapping of the seating to the human body model; and
displaying the calculated performance metrics for the human body model overlaid on an image of the human body model.

20. A system for analyzing automotive seating, comprising:
a pressure sensor having an array of individual pressure sensing elements used to measure pressures on the seating;
a sensor electronics unit in communication with the pressure sensor, the sensor electronics unit receiving the pressure measurements from the pressure sensor; and
a computer in communication with the sensor electronics unit, the computer performing the steps of:
displaying an image of the seating to a user;
providing a user interface to allow the user to graphically locate anchor points on the displayed seating image;
receiving a signal including a location of the anchor points on the pressure sensor;
accessing a pressure map of the pressures measurements;
determining a mapping of locations on the pressure map to locations on the seating, based on the location of the anchor points on the pressure sensor and on the seating image; and
calculating performance metrics for the seating, based on the pressure map and the mapping of the pressure map to the seating.

21. A tangible non-transient computer readable storage medium storing instructions that, when executed, cause a computer system to perform the steps of:
displaying a seating image to a user;
providing a user interface to allow the user to graphically locate anchor points on the displayed seating image;
receiving a signal including a location of the anchor points on a pressure sensor, the pressure sensor having an array of individual pressure sensing elements used to measure pressures on the seating;
accessing a pressure map of the pressures measured by the pressure sensor;
determining a mapping of locations on the pressure map to locations on the seating, based on the location of the anchor points on the pressure sensor and on the seating image; and
calculating performance metrics for the seating, based on the pressure map and the mapping of the pressure map to the seating.

* * * * *